United States Patent [19]
Wang et al.

[11] Patent Number: 5,543,545
[45] Date of Patent: Aug. 6, 1996

[54] METHOD FOR THE PREPARATON OF α-METHYL-β-ACYLTHIOPROPIONATES

[75] Inventors: Shin-Shin Wang; Chih-Hung Chen, both of Hsinchu, Taiwan

[73] Assignee: Industrial Technology Research Institute, Taiwan, Taiwan

[21] Appl. No.: 307,483

[22] Filed: Sep. 16, 1994

Related U.S. Application Data

[63] Continuation of Ser. No. 35,475, Mar. 23, 1993, abandoned.

[51] Int. Cl.$^6$ ............... C07C 327/06; C07C 327/16
[52] U.S. Cl. ............................................. 558/255
[58] Field of Search ................................. 558/255

[56] References Cited

U.S. PATENT DOCUMENTS

| | | | |
|---|---|---|---|
| 4,294,775 | 10/1981 | McKinnie | 558/255 |
| 4,541,959 | 9/1985 | Tomisawa et al. | 558/255 |
| 4,585,595 | 4/1986 | Houbiers | 558/255 |
| 4,681,966 | 7/1987 | Donald et al. | 558/255 |
| 5,149,855 | 9/1992 | Sakimae et al. | 558/255 |

FOREIGN PATENT DOCUMENTS 56-18958  2/1981  Japan.

OTHER PUBLICATIONS

K. Hayashi et al., *Chem. Pharm. Bull.*, vol. 31(2), pp. 570–576, 1983.
S–T. Chen et al., *J.C.S. Chem. Commu.*, pp. 1514–1516, 1986.
S–T. Chen et al., *J. Chem. Res. (s)*, pp. 308–309, 1987.
S–T. Chen et al., *Synthesis*, pp. 581–582, 1987.
S–T. Chen et al., *J.C.S. Chem. Commu.*, pp. 451–458, 1989.

*Primary Examiner*—Michael G. Ramsuer
*Assistant Examiner*—Robert W. Ambrose
*Attorney, Agent, or Firm*—Darby & Darby, P.C.

[57] ABSTRACT

A method is provided for the synthesis of an α-methyl-β-acylthiopropionate of formula I:

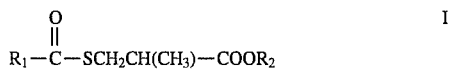

wherein $R_1$ and $R_2$ are independently selected from $C_1$–$C_6$ alkyl, phenyl or substituted phenyl of the formula $C_6H_2R_3R_4R_5$ wherein $R_3$, $R_4$ and $R_5$ are independently selected from hydrogen, lower alkyl, F, Cl, Br, $NO_2$, CN or $R_6O$ wherein $R_6$ is lower alkyl. The method comprises reacting methyl methacrylate with a thiocarboxylic acid at a mole ratio ranging between about 1:1 and about 2:1 and at a temperature ranging between 40° C. and about 150° C. The reaction is conducted either in the presence of an organic solvent or in the presence of polymerization inhibitors for approximately 3 to 6 hours. α-Methyl-β-acyl-thiopropionates are obtained economically by the disclosed method in high purity and yields and in shorter reaction times relative to conventional processes.

12 Claims, No Drawings

METHOD FOR THE PREPARATON OF α-METHYL-β-ACYLTHIOPROPIONATES

This is a continuation of application Ser. No. 08/035,475, filed Mar. 23, 1993, now abandoned.

FIELD AND BACKGROUND OF THE INVENTION

Methyl α-methyl-β-acylthiopropionates are important intermediates for the synthesis of pharmaceutical agents. For instance, Captopril (1-(3-mercapto-2-D-methyl-propanoyl)-L-proline), an orally active angiotensin converting enzyme inhibitor used in treating hypertension, is synthesized from a D-(-)-α-methyl-β-acylthiopropionate.

Methods for preparing α-methyl-β-acylthiopropionates have been reported in the literature. S-T. Chen et al. (1989) *J. Chin. Chem. Soc.*, Vol. 36, pages 451–458, for example, describes preparation of α-methyl-β-acylthiopropionates by an addition reaction between a thiocarboxylic acid, e.g., thiobenzoic acid, with methyl methacrylate. Under the described reaction conditions, however, at least 24 hours is required for the reaction to reach completion and excessive amounts of methyl methacrylate, a toxic reagent, is employed. Accordingly, a simple and economical method for preparing α-methyl-β-acylthiopropionates which eliminates the aforementioned deficiencies is needed in the art.

SUMMARY OF THE INVENTION

The present invention relates to a method for the preparation of α-methyl-β-acylthiopropionates of formula I:

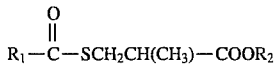

$$R_1-\overset{O}{\underset{\|}{C}}-SCH_2CH(CH_3)-COOR_2 \qquad I$$

wherein $R_1$ and $R_2$ are independently selected from $C_1$-$C_6$ alkyl, phenyl or substituted phenyl of the formula $C_6H_2R_3R_4R_5$ wherein $R_3$, $R_4$ and $R_5$ are independently selected from hydrogen, lower alkyl, F, Cl, Br, $NO_2$, CN or $R_6O$ wherein R6 is lower alkyl.

According to the invention, methyl methacrylate is reacted with a thiocarboxylic acid at a stoichiometric mole ratio (1:1), either in the presence of a suitable organic solvent or in the presence of a suitable polymerization inhibitor, e.g., 4-methoxyphenol, hydroquinone or mixtures thereof. The presence of organic solvent or polymerization inhibitor prevents polymerization of methyl methacrylate, thus the addition reaction may be performed at higher temperatures, e.g. about 40°–150° C., and reach completion at shorter reaction time periods, e.g. about 3 to 6 hours, relative to the conventional process (approximately 24 hours at room temperature). α-Methyl-β-acylthiopropionates are obtained by the inventive method in high yields and purity (>90%), shorter reaction periods and at a lower cost.

DETAILED DESCRIPTION OF THE INVENTION

All patents, patent applications and literature references cited herein are hereby incorporated by reference in their entirety.

According the method of the invention, formula I α-methyl-β-acylthiopropionate is obtained by reacting a methyl methacrylate defined by formula III with a thiocarboxylic acid defined by formula II:

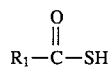

$$R_1-\overset{O}{\underset{\|}{C}}-SH \qquad II$$

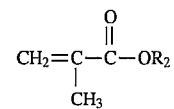

$$CH_2=\underset{\underset{CH_3}{|}}{C}-\overset{O}{\underset{\|}{C}}-OR_2 \qquad III$$

wherein $R_1$ and $R_2$ are independently selected from $C_1$-$C_6$ alkyl, phenyl or substituted phenyl of the formula $C_6H_2R_3R_4R_5$ wherein $R_3$, $R_4$ and $R_5$ are independently selected from hydrogen, lower alkyl, F, Cl, Br, $NO_2$, CN or $R_6O$ wherein R6 is lower alkyl. Representative examples of substituted phenyls include 4-methylphenyl, 2-t-butylphenyl and 2,6-dichlorophenyl.

Methyl methacrylate is added to a thiocarboxylic acid at a mole ratio ranging between about 1:1 and about 2:1. In practicing the invention, it is preferable to use a stoichiometric equivalent amount of methyl methacrylate. The rate of methyl methacrylate addition generally ranges between about 0.3 to about 1.0 mL per minute, preferably between about 0.5 and about 0.7 mL per minute. If methyl methacrylate is added to thiocarboxylic acid in one portion, lower yields of product are obtained and polymeric material is produced. Prior to addition, the thiocarboxylic acid is preheated to a temperature ranging between about 40° C. and about 150° C., preferably ranging between about 80° C. and about 90° C.

Upon completion of the addition, the reaction mixture is maintained at within the aforementioned temperature range for a time period ranging between about 3 and about 19 hours, preferably ranging between about 3 and about 6 hours.

In one embodiment of the invention, methyl methacrylate is added to a solution of a thiocarboxylic acid and a suitable organic solvent under the aforementioned reaction conditions. The volume of solvent generally ranges between about 10 to about 50 mL, preferably ranging between about 15 and about 20 mL per 12.3 mL of thiocarboxylic acid.

Suitable, but non-limiting, examples of solvents include ethers such as tetrahydrofuran, dioxane and isopropyl ether; alcohols such as isopropanol, t-butanol, and 2-methylpropanol; ketones such as acetone and methylethylketone; esters such as ethyl acetate and t-butyl acetate; chlorinated solvents such as dichloromethane, 1,2-dichloroethane and chloroform; and aromatic solvents such as toluene and xylene. In practicing this invention, the preferred solvents are toluene, ethylacetate and isopropyl alcohol.

In another embodiment of the invention, methyl methacrylate is added to a thiocarboxylic acid in the presence of a polymerization inhibitor and without added solvent. The reaction conditions are the same as described above. The amount of polymerization inhibitor generally ranges between about 0.01 and about 0.001 mole, preferably ranging between about 0.004 and about 0.005 mole per mole of thiocarboxylic acid.

Suitable, but non-limiting examples of polymerization inhibitor agents include 4-methoxyphenol, hydroquinone and mixtures thereof. In practicing this invention, hydroquinone as polymerization inhibitor agent is preferred.

When the reaction reaches completion, as determined by gas chromatography or other suitable method, conventional organic chemistry procedures for the extraction and purification of α-methyl-β-acylthiopropionate from the reaction mixture are then performed. For example, the reaction mixture is extracted with a suitable organic solvent, e.g., ethyl acetate, and the extracts are washed with water, optional aqueous alkaline solution, e.g., 2N NaOH, and brine. Thereafter, the extracts are dried over a suitable drying agent such as sodium sulfate. Removal of the drying agent and solvent affords α-methyl-β-acylthiopropionates in yields generally above 90% and with purities typically exceeding 95%.

The present invention provides a simple and economical method for preparing α-methyl-β-acylthiopropionate in higher yields and shorter reaction times relative to conventional processes and further without polymerization impurities. If desired, optically active forms of α-methyl-β-acylthiopropionates produced by the method of the invention may be isolated by conventional resolution methods.

The following example illustrates the invention but does not serve to limit its scope.

THE PREPARATION OF α-METHYL-β-BENZOLYTHIOPROPIONATE (A) Solvent Method

In a 50 mL three-necked reaction flask, 10.7 mL (0.107 mole) of methyl methacrylate was added dropwise over a 22 minute period to a pre-heated (80° C.) solution of 12.3 mL (0.105 mole) of thiobenzoic acid and 20 mL toluene. Thereafter, the reaction mixture was maintained at reflux for an additional 3 hours. The resulting reaction mixture was then cooled to room temperature, diluted with 120 mL ethyl acetate, washed with water (1x25 mL), 5% sodium bicarbonate (3x25 mL), brine (2x35 mL) and dried over anhydrous sodium sulfate. The solvent was removed under reduced pressure to afford 22.35 g of colorless oil product (94% yield). The purity (99%) and structural identity was confirmed by GC, $^1$HNMR, $^{13}$CNMR and mass spectroscopy.

(B) Polymerization Inhibitor Method

In a 25 mL three-necked reaction flask, 10.7 mL (0.107 mole) of methyl methacrylate was added dropwise over a 22 minute period to a pre-heated mixture (80° C.) of 12.3 mL (0.105 mole) of thiobenzoic acid and 0.55 g (0.005 mole) hydroquinone. Thereafter, the reaction mixture was maintained at 80°–85° C. for additional 6 hours. The resulting reaction mixture was diluted with 150 mL ethyl acetate, washed with water (1x25 mL), 2N NaOH solution (4x25 mL), brine (2x25 mL), and dried over anhydrous $Na_2SO_4$. The solvent was removed under reduced pressure to afford 23.22 g of a colorless oil product (97% yield). The purity (99%) was determined by GC.

Table I summarizes the yields and GC analysis results for preparation of α-methyl-β-acylthiopropionate in the presence of various organic solvents or in the presence of polymerization inhibitors. As shown in Table I, incorporation of a solvent or polymerization inhibitor in the addition reaction results in the production of α-methyl-β-acylthiopropionate in excellent yields and purity.

TABLE I

| Preparation of α-methyl-β-benzoylthiopropionate | | | | |
|---|---|---|---|---|
| Temperature | Solvent | Inhibitor | Purity[a] (%) | Yield (%) |
| reflux | THF | — | 97 | 95 |
| reflux | isopropanol | — | 98 | 88 |
| reflux | dioxane | — | 99 | 92 |
| reflux | acetone | — | 99 | 72 |
| reflux | ethyl acetate | — | 99 | 91 |

TABLE I-continued

| Preparation of α-methyl-β-benzoylthiopropionate | | | | |
|---|---|---|---|---|
| Temperature | Solvent | Inhibitor | Purity[a] (%) | Yield (%) |
| reflux | toluene | — | 99 | 94 |
| reflux | t-butanol | — | 99 | 92 |
| reflux | dichloromethane[b] | — | 99 | 96 |
| 80–85° C. | — | 4-methoxyphenol | 96 | 97 |
| 80–85° C. | — | hydroquinone | 99 | 97 |

[a]The purity of product was determined by GC.
[b]When dichloromethane solvent is used, the reaction requires 19 hours to reach completion. In contrast, the other reactions in this table typically require only 3–6 hours to reach completion. The boiling point of dichloromethane is lower than that of other solvents, so a longer reaction time is needed to complete the reaction.

What is claimed:

1. A method for the preparation of an α-methyl-β-acylthiopropionate of formula I:

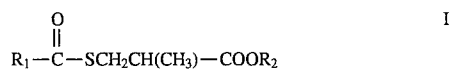

wherein $R_1$ and $R_2$ are independently selected from $C_1$–$C_6$ alkyl, phenyl or substituted phenyl of the formula $C_6H_2R_3R_4R_5$ wherein $R_3$, $R_4$ and $R_5$ are independently selected from hydrogen, lower alkyl, F, Cl, Br, $NO_2$, CN or $R_6O$ wherein $R_6$ is lower alkyl, said method comprising reacting a thiocarboxylic acid of formula II with a methacrylate ester of formula (III):

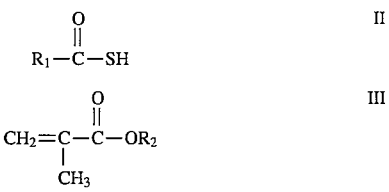

wherein $R_1$ and $R_2$ are as defined above, in the presence of an organic solvent or in the presence of a polymerization inhibitor at a reaction temperature ranging between about 40° C. and about 150° C. and at a mole ratio of thiocarboxylic acid to methacrylate ester ranging between about 1:1 and about 1:2;

wherein the rate of methacrylate ester addition is from about 0.3 to about 1.0 mL per minute; and wherein the thiocarboxylic acid is pre-heated to a temperature of from about 40° C. to about 150° C. prior to the addition of the methacrylate ester.

2. The method according to claim 1, wherein the molar ratio between the thiocarboxylic acid and the methyl methacrylate is about 1:1.

3. The method according to claim 1, wherein said organic solvent comprises tetrahydrofuran, isopropyl alcohol, dioxane, acetone, ethyl acetate, t-butanol, toluene, benzene, dichloromethane or mixtures thereof.

4. The method according to claim 3, wherein the reaction is maintained under reflux.

5. The method according to claim 1, wherein said polymerization inhibitor comprises 4-methoxyphenol, hydroquinone or mixtures thereof.

6. The method according to claim 5, wherein the reaction is maintained at a temperature ranging from about 80° to about 85° C.

7. The method according to claim 1, wherein said substituted phenyl comprises 4-methylphenyl, 2-t-butylphenyl or 2,6-dichlorophenyl.

8. The method according to claim 1, wherein the rate of methacrylate ester addition is from about 0.5 to about 0.7 mL per minute.

9. The method according to claim 1, wherein the thiocarboxylic acid is pre-heated to temperature of from about 80° C. to about 90° C.

10. The method according to claim 1, wherein the amount of polymerization inhibitor is from about 0.01 to about 0.001 mole per mole of thiocarboxylic acid.

11. The method of claim 1 wherein said thiocarboxylic acid and said methacrylate ester are reacted in the presence of an organic solvent.

12. The method of claim 1 wherein said thiocarboxylic acid and said methacrylate ester are reacted in the presence of a polymerization inhibitor.

* * * * *